(12) United States Patent
Tans

(10) Patent No.: US 7,597,014 B2
(45) Date of Patent: Oct. 6, 2009

(54) SYSTEM AND METHOD FOR PROVIDING VERTICAL PROFILE MEASUREMENTS OF ATMOSPHERIC GASES

(75) Inventor: Pieter P. Tans, Boulder, CO (US)

(73) Assignee: The United States of America as represented by the Secretary of Commerce, Washington, DC (US)

( * ) Notice: Subject to any disclaimer, the term of this patent is extended or adjusted under 35 U.S.C. 154(b) by 483 days.

(21) Appl. No.: 11/464,607

(22) Filed: Aug. 15, 2006

(65) Prior Publication Data

US 2008/0041171 A1 Feb. 21, 2008

(51) Int. Cl.
G01N 1/12 (2006.01)
(52) U.S. Cl. .................................. 73/864.51
(58) Field of Classification Search .............. None
See application file for complete search history.

(56) References Cited

U.S. PATENT DOCUMENTS

| | | | | |
|---|---|---|---|---|
| 2,943,490 | A * | 7/1960 | Melton | 73/864.31 |
| 3,063,296 | A * | 11/1962 | Huch et al. | 73/864.31 |
| 3,077,779 | A * | 2/1963 | Froehlich et al. | 73/864.91 |
| 3,355,940 | A | 12/1967 | Pannetier | |
| 3,499,326 | A * | 3/1970 | Pannetier et al. | 73/863.23 |
| 3,521,493 | A | 7/1970 | Guizouam | |
| 3,858,573 | A * | 1/1975 | Ryan et al. | 600/543 |
| 3,938,367 | A | 2/1976 | Fletcher | |
| 4,019,863 | A * | 4/1977 | Jenkins et al. | 250/304 |
| 4,170,901 | A | 10/1979 | Conkle | |
| 4,226,115 | A | 10/1980 | Williams | |
| 4,283,948 | A * | 8/1981 | Longsworth | 73/863.11 |
| 4,499,930 | A | 2/1985 | Walters | |
| 4,584,887 | A * | 4/1986 | Galen | 73/863.31 |
| 5,404,763 | A | 4/1995 | Guggenheim | |
| 5,410,918 | A * | 5/1995 | Zimmerman | 73/864 |
| 5,553,508 | A | 9/1996 | Dabberdt | |
| 5,834,656 | A * | 11/1998 | Seltzer | 73/863.71 |
| 6,477,906 | B1 * | 11/2002 | Peterson | 73/863.21 |
| 7,096,749 | B2 * | 8/2006 | Schimmoller et al. | 73/863.21 |
| 7,159,475 | B2 * | 1/2007 | Casillas et al. | 73/864.34 |

\* cited by examiner

*Primary Examiner*—Robert R Raevis
(74) *Attorney, Agent, or Firm*—Jeffrey D. Moy; Veronica-Adele R. Cao; Weiss & Moy, P.C.

(57) ABSTRACT

A system and method for using an air collection device to collect a continuous air sample as the device descends through the atmosphere are provided. The air collection device may be one or more coils of thin-walled elongated hollow tubing having a small interior diameter. The thin-walled elongated hollow tubing may be of a substantially nonreactive and nonabsorptive material such as stainless steel. A valve or the like controls the flow of air into and out of the tubing with one of the ends of the tubing closed and the other of the ends open at the beginning or end of the ascent and closed substantially at the end of the descent to seal the continuous air sample in the air collection device. The air collection device may be insulated and have cushioning.

Once the continuous air sample is collected in the air collection device, it is analyzed to determine the presence and mole fraction of trace gases at different altitudes in the atmosphere. A high resolution continuous vertical profile of the trace gas may be created.

The air collection device may also be used to store a sample gas using a compressor which draws or pushes the gas into the air collection device over a selected period of time. The stored gas may be analyzed in the same manner as the atmospheric air to obtain a time history of the gas sample.

12 Claims, 8 Drawing Sheets

SYSTEM AND METHOD FOR PROVIDING VERTICAL PROFILE MEASUREMENTS OF ATMOSPHERIC GASES

FIELD OF THE INVENTION

This invention relates generally to the Earth's atmospheric system. More specifically, this invention relates to a system and method for providing high resolution, in-situ vertical profile measurements of atmospheric trace gases.

BACKGROUND OF THE INVENTION

Global warming is a popular term used to describe the increase in average global temperatures due to the greenhouse effect. Global warming has occurred in the distant past as the result of natural influences, but the term is most often used to refer to the warming predicted to occur as a result of increased emissions of greenhouse gases. Global warming is thought to cause severe increases in Earth's atmospheric and surface temperatures, with disastrous environmental consequences such as changes in weather, sea levels, and land use patterns, commonly referred to as "climate change." Global warming is claimed to be so dangerous that it makes necessary a dramatic reduction in the burning of fossil fuels and a massive program to restructure our energy supply system.

Levels of several important greenhouse gases have increased by about 35 percent or more since large-scale industrialization began around 150 years ago. Some greenhouse gases occur naturally in the atmosphere, while others result from human activities. Naturally occuring greenhouse gases include water vapor, carbon dioxide, methane, nitrous oxide, and ozone. In addition, very powerful greenhouse gases that are not naturally occurring include chlorofluorocarbons (CFCs), hydrofluorocarbons (HFCs), perfluorocarbons (PFCs), and sulfur hexafluoride (SF6), which are generated in a variety of industrial processes. Other trace gases include carbon monoxide, hydrogen, HCFC-22, HCFC-141b, methyl halides, methyl chloroform, dichloromethane, chloroform, tetrachloroethylene, halons, bromoform, carbonyl sulfide, ethane, ethene, propane, propene, (i,n)-butane, butanes, acetylene, (i,n)-pentane or the like. Carbon dioxide, emitted by the combustion of fossil fuels such as coal, oil and gasoline, is the most abundant greenhouse gas after water vapor. As used herein, "greenhouse gases" are synonymous with "trace gases", except water vapor which is not considered further because its concentration is fully determined by the climate system itself, not by human action directly.

Climate change induced by increasing mole fractions of various atmospheric constituents is a matter of immense importance. There is uncertainty in how the climate system varies naturally and reacts to emissions of greenhouse gases. Making progress in reducing uncertainties in projections of future climate requires better awareness and understanding of the buildup of greenhouse gases in the atmosphere and the behavior of the climate system. For effective management, a solid scientific understanding of their natural cycles and the processes that influence those cycles is necessary. To slow the rate of anthropogenic-induced climate change in the 21st century and to minimize its eventual magnitude, societies will need to manage the climate forcing factors that are directly influenced by human activities, in particular greenhouse gas and aerosol emissions. Precise and accurate atmospheric measurements are the touchstone of theories or models describing these cycles. Measurement data may be used to identify long-term trends, seasonal variability, and spatial distribution of greenhouse gases. Vertical profiles are an extremely important part of atmospheric science and gauge the gases' vertical journey as they rise from the Earth's surface into the upper atmosphere or vice versa. These "vertical profiles" can be used to test biogeochemical models of CO2, CH4, N20 and other gases that drive climate change. Vertical measurements show where the trace gas is in the atmosphere (i.e. at what height or altitude) and the quantity of trace gas in the atmosphere (its mole fraction, expressed as parts per million or parts per billion).

In addition, accurate and long-term records of atmospheric gases help advance global and regional environmental information and services regarding ozone depletion and baseline air quality.

The conventional approach to acquiring atmospheric samples for laboratory analysis is to use flask sampling. This is done by taking flask samples at different points in the atmosphere and bringing these flasks to a laboratory for precise mole fraction measurement of gaseous constituents. While good for point sampling, flask sampling requires multiple flasks and complicated sampling to acquire profile data. The complicated sampling requires opening each individual flask at the desired location in the atmosphere, collecting the sample, and closing each individual flask while moving through the atmosphere. Also, each of the flasks must be analyzed individually which increases the cost. For each doubling of the resolution requirement, i.e. resolution value halved, the number of flasks doubles and the number of analysis steps for the laboratory analysis also doubles. This greatly increases the cost of high resolution gas mole fraction profile measurements.

There are other ways of directly measuring atmospheric constituents. For example, laboratory equipment may be taken into the field on a stationary platform and measurements taken at a single point. There are generally two known techniques that may be used to measure the mole fraction of greenhouse gases: absorption of infrared light or by gas chromatography potentially followed by mass spectroscopy. Alternatively, measurement equipment may be placed on a mobile platform and measurements taken as the platform moves through the atmosphere. Unfortunately, the results obtained from these non-laboratory field condition tests are imprecise and inaccurate, difficult to obtain, and generally do not provide sufficient vertical resolution.

Accordingly, there has been a need for a system and method that reduce the costs associated with and simplify the acquisition of in-situ high resolution gas mole fraction profile measurements. There is also a need for a system and method that provide precise and accurate measurements, with improved resolution. There is also a need for a system and method which do not become appreciably more expensive as the vertical resolution increases. There is also a need for a system and method that do not require complicated configuration changes and sampling techniques. The present invention fulfills these needs and provides other related advantages.

SUMMARY OF THE INVENTION

The present invention in a first embodiment resides in a system and method for measuring the mole fraction of trace gases in the atmosphere. The system and method are simple to use, and provide superior high resolution measurements. The system and method show a continuous profile in the vertical rather than a single sample at one altitude.

The system comprises, generally, an air collection device for collecting a continuous air sample at different altitudes, the air collection device comprised of elongated hollow tubing having a small internal diameter and closure means at each of the ends thereof for controlling the flow of air into and out of the air collection device; and one or more analytical instruments in fluid communication with one end of the air collection device and a source of calibrated air in fluid communication with the other end thereof, the calibrated air gradually pushing the continuous air sample out of the air collection device into the one or more analytical instruments for providing vertical profile measurements of the at least one trace gas in the continuous air sample.

The elongated hollow tubing has the following preferred approximate dimensions (in inches):

|        | Minimum | Maximum | Preferred     |
|--------|---------|---------|---------------|
| id     | 0.230   | 0.355   | 0.230         |
| od     | 0.250   | 0.375   | 0.250         |
| wt     | 0.010   | 0.028   | 0.010         |
| length | 50 m    | 300 m   | 150 m or more | id = inner diameter;
od = outer diameter;
wt = wall thickness

The tubing may be coiled and comprised of a substantially nonabsorptive and nonreactive material. A preferred material for the coiled elongated tubing is stainless steel. The closure means may be valves, endcaps or the like.

The air collection device may be launched or carried into the atmosphere. The air collection device may be insulated for flight to maintain a substantially constant temperature during its ascent and descent. The air collection device may further include cushioning to shield the air collection device from impact forces during landing.

The ends are normally closed. One of the ends is opened either just before ascent or just before descent. As the air collection device ascends to maximum altitude, the air within the tubing evacuates. As the air collection device descends from the high altitudes and low pressure (i.e. moves from low pressure to high pressure), a continuous ambient air sample is forced into the open end of the insulated air collection device and compressed by the air entering later at lower altitudes. The air from lower pressure regions will move closer to the closed end of the air collection device. As soon as possible after the air collection device lands, the one open end is closed sealing the continuous air sample into the air collection device, completing the collection step.

The air collected in the air collection device is then analyzed by the one or more analytical instruments to determine the presence and mole fraction of trace gases therein.

In another embodiment, the air collection device may be used to store a time history of a sample gas. A pump or compressor may be used to slowly draw or push the gas sample into one end of the air collection device. The other end is also open. Once the gas is collected, it may be stored in the air collection device by closing the ends thereof. The sample gas may be analyzed in the same manner as the atmospheric air collected in the air collection device to obtain a time history of the stored gas.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
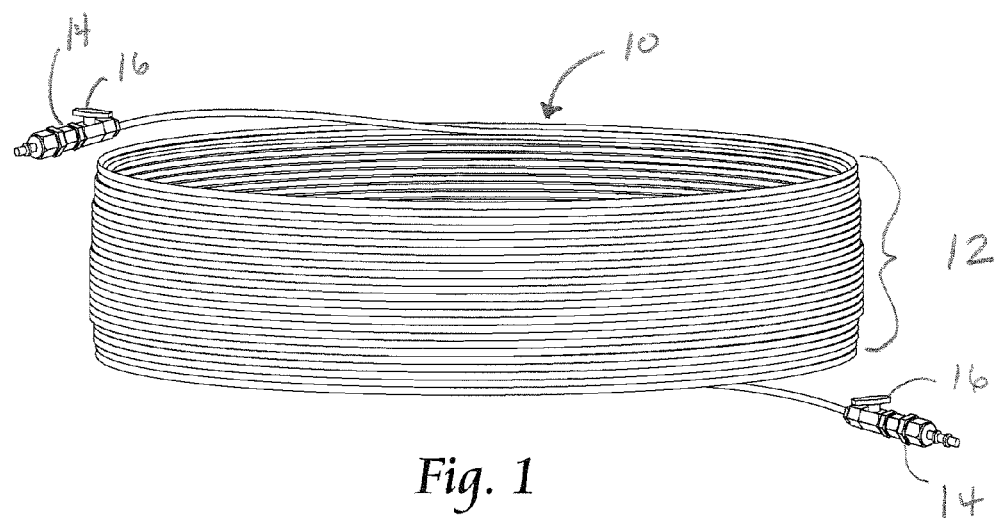
FIG. 1 is a perspective view of an air collection device embodying the invention, illustrating coiled small diameter elongated hollow tubing with an exemplary valve at each end of the tubing.

As shown in the drawings for purposes of illustration, the present invention is concerned with an improved system and method for providing high resolution in situ vertical profile measurements of trace gases in the atmosphere comprising, generally, the steps of collecting a continuous air sample using an air collection device and analyzing the collected continuous air sample for trace gases. The air collection device is generally designated in the accompanying drawings by the reference number 10. Referring to FIG. 1, the air collection device comprises, generally, one or more coils of small diameter elongated hollow tubing 12 having two open ends (not shown), and a valve 14 at each of the two open ends for controlling the flow of air into and out of the tubing 12.

In accordance with the present invention, and as illustrated with respect to a preferred embodiment in FIGS. 1 through 6, the air collection device 10 may be launched or carried into the atmosphere and collects air from different altitudes as it descends. The ends are normally closed. The valve at the bottom of the coil may be opened either just before ascent or just before descent to inlet air and closed at the substantial completion of the descent to seal the continuous air sample in the air collection device 10.

The elongated hollow tubing 12 has a length ranging from about 50 m to about 300 m, preferably 150 m or more. The longer the air collection device, the greater the vertical resolution i.e. how much the trace gas mole fraction changes in the vertical. If the mole fraction is changing quickly, the better resolution allows for more reference points in the vertical. "Mole fraction" as defined herein is the quantity of trace gas per quantity of whole air.

The elongated hollow tubing 12 has the following preferred approximate dimensions (in inches):

|    | Minimum | Maximum | Preferred |
|----|---------|---------|-----------|
| id | 0.230   | 0.355   | 0.230     |
| od | 0.250   | 0.375   | 0.250     |
| wt | 0.010   | 0.028   | 0.010     | id = inner diameter;
od = outer diameter;
wt = wall thickness

The tubing cross section is typically round, although other shapes may be used. The diameter and shape of the tubing may be uniform throughout the air collection device or have sections with varying diameters and shapes within the ranges above.

Coiled elongated tubing is easier to handle and transport, but it is to be appreciated that uncoiled elongated tubing may be used. Coiled tubing in long lengths either is available in single coils or multiple coils orbitally welded together. A coil is a structure consisting of something wound in a continuous series of loops, i.e. a spiral of elongated tubing as shown in FIG. 1.

The tubing 12 may be available in a variety of different materials that are substantially nonabsorptive and nonreactive with the trace gases. The material used may not absorb or emit a significant amount of the gas being measured. Suitable materials include stainless steel, titanium, Dekabon, which is a light weight aluminum and polyethylene laminate, or other nonabsorptive and nonreactive material. Suitable stainless steel tubing may be available from Eagle Stainless Tube and Fabrication, Inc., 10 Discovery Way, Franklin, Mass. 02038, among other manufacturers. A coating may be applied to the inside of the tubing to increase its inertness (or nonreactivity). For example, Restek, Inc. may apply its Silcosteel process to apply a thin layer of silicate on the inside of the stainless steel tubing. The inside of the stainless steel tubing may be coated with other nonreactive coatings including glass, nickel, gold or the like.

A preferred coiled air collection device 10 is about 6 mm in diameter×150 m long comprised of stainless steel. Although exemplary air collection devices having specific lengths, diameters and compositions have been described, it is to be appreciated that more research needs to be completed on optimizing the length, diameter and composition of the coils to preserve records of different gases of interest and such examples are not intended to be limiting.

The valve 14 at each end of the elongated tubing may each include a lever 16 to open and close the valve at the respective end of the tubing for purposes as hereinafter described. While valves are shown as the preferred closure means, it is to be appreciated that substantial benefit may be achieved by the use of closure means other than valves, for example, by removable endcaps or the like. The closure means may be operated manually or automatically.

In the method of the invention, the collection step includes launching the air collection device by balloon, aircraft or the like, or the air collection device may remain on board the aircraft during the entire flight, and be removed after landing. The air collection device is transported to a maximum selected altitude before descent. Tracking of the air collection device during balloon flight is done by known means, for example, by a GPS tracker 20 or the like.

Figure 5:
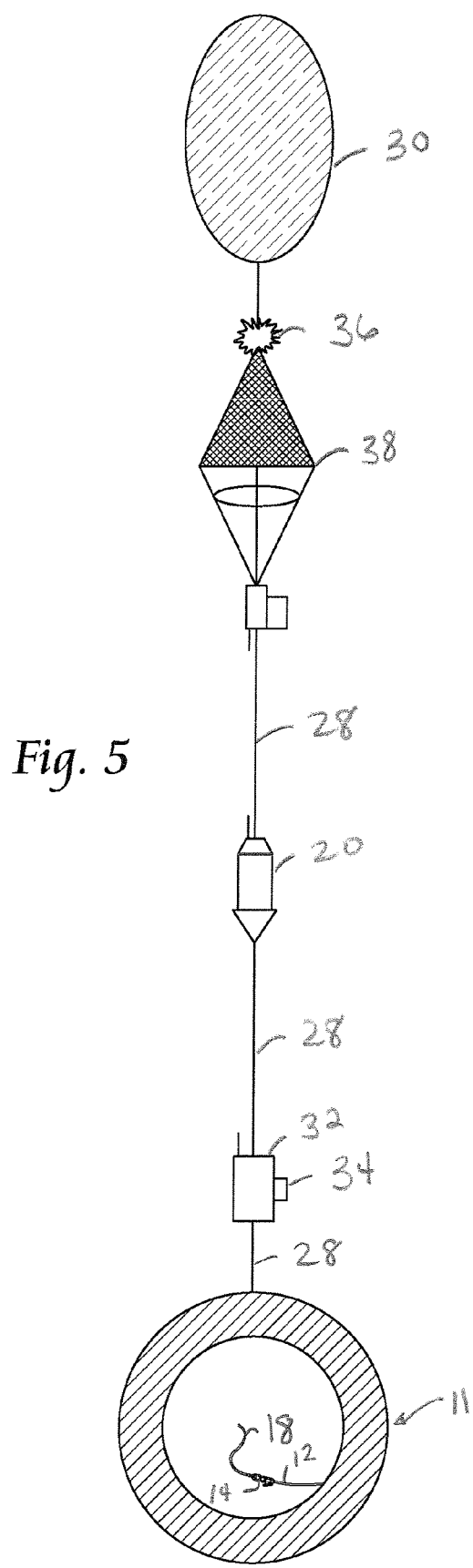
FIG. 5 is a schematic view of another exemplary balloon-launched assembly for an insulated air collection device, illustrating an inlet valve at the bottom of the air collection device with a removable plastic tube (not shown) coupled thereto.

Referring to FIG. 5, a balloon-launched air collection device may further comprise a plastic tube 18 removably coupled to the inlet side of the valve at the bottom of the coil to substantially prevent dirt and other debris from contaminating the collected air sample at impact upon landing. The valve at the bottom of the coil is the valve that is opened either just before ascent or descent to inlet air and closed at the substantial completion of the descent to seal the continous air sample in the air collection device 10.

Figure 3:
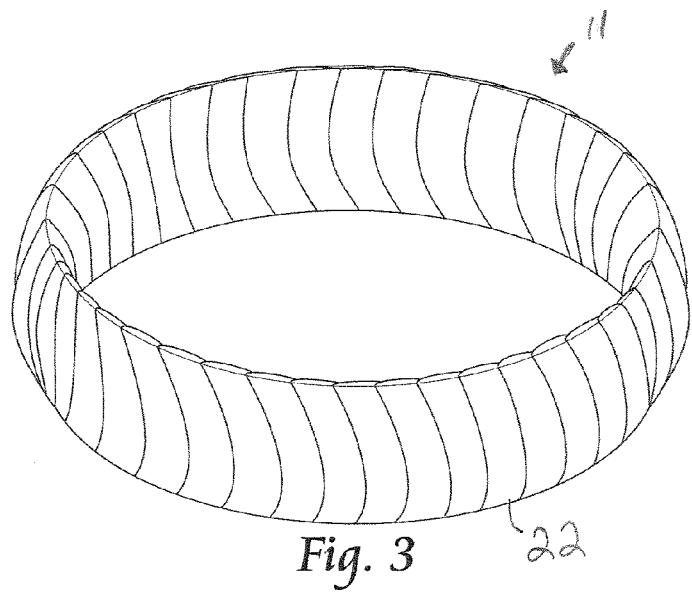
FIG. 3 is a perspective view of an insulated air collection device, illustrating the air collection device of FIG. 1 (without valves) wrapped with insulation.
Figure 4:
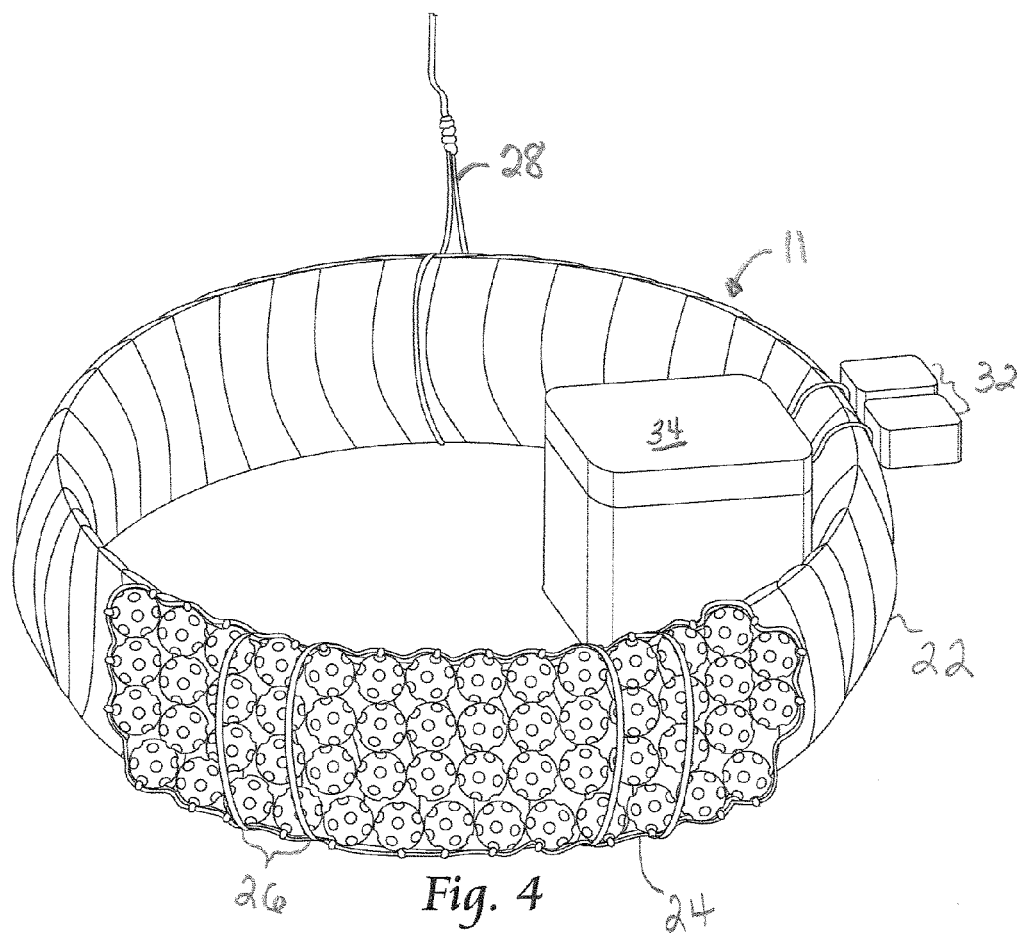
FIG. 4 is a perspective view of an exemplary balloon-launched assembly for the insulated air collection device of FIG. 3, illustrating the insulated air collection device attached by a line to a balloon (not shown) with the exemplary impact absorber of FIG. 2 coupled to a bottom portion of the insulated air collection device, and a data collection device and data recording equipment coupled to the insulated air collection device.

For flight (whether by launch or being carried on board), the air collection device 10 may further comprise insulation 22 which can serve as the outermost covering of the air collection device as shown in FIGS. 3 and 4. The air collection device with the insulation is hereinafter referred to as "an insulated air collection device" and designated in the accompanying drawings by the reference number 11. The insulation may be used to maintain a substantially constant temperature during ascent and descent of the air collection device as hereinafter described. The insulation should not emit a significant amount of gas to avoid contaminating the air pulled into coil. The insulating material may be reflective of sunlight and therefore white insulating material is preferred. A suitable insulating material is 1/8" Volaraa Closed Cell Foam (099-5247) manufactured by Advanced Materials, Inc., P.O. Box 974-680, Dallas, Tex. 75397 but substantial benefit may be derived from other insulating materials. The insulation may be in the form of a sleeve or wrap as shown in FIGS. 3-4. The insulation may be held in place with standard white plastic tape or the like if necessary.

Figure 2:
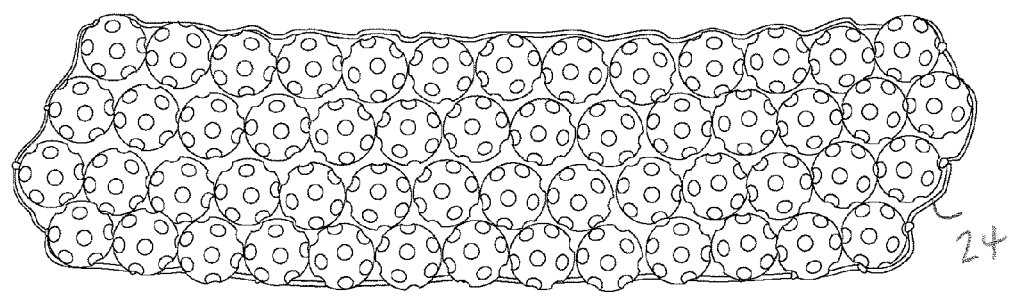
FIG. 2 is an enlarged view of a portion of an exemplary impact absorber for the air collection device.

Referring to FIG. 4, the insulated air collection device 11 may further comprise an impact absorber 24 to cushion the insulated air collection device upon landing. The impact absorber may be coupled to the bottom exterior surface of the insulated air collection device by ties 26 or the like. An exemplary impact absorber is shown in FIGS. 2 and 4, although it is to be appreciated that other impact absorbers may be used within the confines of the invention. The exemplary impact absorber comprises a plurality of practice golf balls tied together as hereinafter described. Cushion means coupled to the sides of the insulated air collection device may also be used to protect the sides thereof. While a separate impact absorber has been described, substantial benefit may be achieved by incorporating the impact absorber into the insulation.

Exemplary balloon-launched air collection assemblies are shown in FIGS. 4 and 5. The insulated air collection device 11 may be tied or connected by a line of nylon cord 28 or the like to a helium or hydrogen filled balloon 30, which lifts the air collection device up through the atmosphere. The length of the line may be selected to separate the various payloads as hereinafter described so they will not interfere with each other physically or electrically. A payload is an individual container or box that carries equipment for some purpose associated with the flight.

The maximum altitude the balloon ascends to is determined by the size of the balloon, or weight of the balloon material. Balloon sizes may typically range from about 150 grams to about 3000 grams of latex rubber. The size of the balloon is selected based on the total weight of all the payloads to be carried up. The heavier the payload(s), the greater the size of the balloon. For total payload weight of 20-25 pounds, a 3000 gram balloon may be used to reach altitudes of 60,000 to 90,000 feet. A 3000 gram latex balloon with a 20-25 pound payload will generally burst at between 60,000 and 90,000 feet due to a combination of external air pressure and ultraviolet radiation at that altitude.

Referring to FIG. 4, the insulated air collection device 11 may be connected to a data collection device 32. The variables measured by the data collection device may include: pressure, altitude, geographical position (latitude/longitude), temperature, and relative humidity. The data collection device may also be connected to data recording equipment 34 including batteries, temperature sensors, and the like. As shown in FIG. 4, the data collection device 32 and data recording equipment 34 may be attached to the insulated air collection device 11 to get the most correct readings of the air entering the open end of the air collection device. Alternatively, the data collection device 32 and data recording equipment 34 may be attached to the balloon line 28 as shown in FIG. 5. In both embodiments, the balloon line may further include the GPS tracker 20, a "cut down" device 36 to separate the lower payloads from the balloon if necessary, and a parachute 38 below the balloon 30 as also shown in FIG. 5. After bursting of the balloon 30, the air collection device will descend through the atmosphere aided by the parachute 38 (FIG. 5). The size of the parachute 38 may be based on the total weight of the payloads to be brought down and the desired descent rate as is known by one skilled in the art. The payloads shown in FIGS. 4 and 5 include the insulated air collection device 10, the data collection device 32, the data recording equipment 34, the GPS tracker 20, the "cut down" device 36 and the parachute 38, the total weight of which is considered for sizing the balloon and the parachute.

The insulated air collection device 11 may also be carried aloft by aircraft (not shown) including conventional small airplanes, commercial airliners or by high-altitude manned and unmanned research aircraft, and from Unmanned Aircraft System (UAS) platforms. When being carried by aircraft, the impact absorber 24 may be unnecessary. Additionally, there may not be a data collection device 32 and/or data recording equipment 36 on the air collection device as the aircraft system may provide the necessary environmental information.

The insulated air collection device 11 may be transported to a suitably high altitude (i.e. a "maximum altitude") and then returned to the surface of the earth by a known path. The ends of the air collection device are normally in the closed position whether by turning the lever 16 on the respective valve to the closed position, positioning of an endcap thereon, or the like. One of the ends of the air collection device is opened at the beginning of the ascent, or at the highest point just before descent, either by hand or automatically by turning the respective valve lever to the open position, removing the respective endcap or the like. The valve operation may be done remotely.

As the insulated air collection device ascends to maximum altitude, the air within the tubing 12 evacuates out the open end of the insulated air collection device and into the plastic tube 18 before exiting into the atmosphere. During descent of the insulated air collection device, the air flows into the open end of the plastic tube 18, through the open valve and then into the air collection device 10. As the insulated air collection device descends from high altitudes and low pressure, a continuous ambient air sample is forced into the open end of the air collection device and compressed by the air entering later at lower altitudes. As the air collection device moves from low pressure to high pressure, a continuous ambient air sample will flow into the open end of the air collection device and flow part way toward the closed end. The air from lower pressure regions will move closer to the closed end of the air collection device. As soon as possible after the insulated air collection device lands, the one open end is closed by closing the valve, replacing the endcap or the like, either by hand or automatically so that the air collection device contains a sample "core" of the atmosphere. This completes the collection step.

The rate of inflow into the air collection device 10 is determined by the rate of descent, the outside air temperature and the temperature of the air collection device. The position in the air collection device, determined by the history of pressure versus outside air temperature and air collection device temperature defines the altitude at which the air is sampled. The rate of air flow into the device is given to an excellent approximation by the mass balance equation (which assumes that the coil has uniform diameter along its entire length):
$L \times d(\rho_{coil})/dt = \rho_{atm} \times v$ in which
L=length of tube (fixed)
$\rho_{coil}$=density of air inside the coil
d/dt=the time derivative of the above
$\rho_{atm}$=density of the outside air entering tube
v=velocity of the entering air The ambient air from different altitudes remains substantially unmixed. The relative slowness of diffusion of air in the direction of the long dimension of the tube or coil being filled from one end preserves the history of the mole fraction as the air enters the tubing. Therefore, the air collection device retains a measure of what was ingested first and what was ingested later, allowing profile measurements.

At the scale sizes association with the size of the air collection device, the free atmosphere is characterized by homogenous, isotropic turbulence. Specifically, the inner diameter of the air collection device is much smaller than the existing turbulent eddies, i.e. the wave number of the isotropic turbulence that can exist in the tubing is well beyond the inner scale of turbulence and is in the viscous subrange of the spectrum of turbulence where turbulent mechanical energy has been dissipated (and converted to heat) by atmospheric viscosity. This means that there is substantially no turbulent diffusion within the tubing (as there is no turbulent energy within the tubing) and that the only diffusion is due to molecular diffusion. Some mixing occurs during the filling and "read out" as hereinafter described because of the laminar flow velocity profile inside the tubing. The tubing diameter is small, so that diffusion in the small radial direction is effective in evening out such differences. The typical rate of descent through the atmosphere is low so the flow is laminar. This is almost always the case since the pressure difference between the open end of the tubing and the closed end of the tubing is very small. The system and method permit sampling at many points in the vertical by not allowing the sample of gas to be well-mixed. The air collection device and method shows a continuous profile in the vertical rather than a single sample at one altitude.

The analyzing step comprises analyzing the contents of the air collection device with suitable equipment to determine the profile of the mole fraction of a specific gas. Measurable trace gases include CO2, methane, nitrous oxide, sulfur hexafluoride, carbon monoxide, hydrogen or the like. Other candidates include CFSs (CFC-11, CFC-12, CFC-113, and CFC-114), HFC-134a, HCFC-22, HCFC-141b, methyl halides, methyl chloroform, dichloromethane, chloroform, tetrachloroethylene, halons, bromoform, carbonyl sulfide, ethane, ethene, propane, propene, (i,n)-butane, butanes, acetylene, (i,n)-pentane or the like. This listing is not intended to be an exhaustive list of trace gases that may be measured by the present invention.

Figure 6:
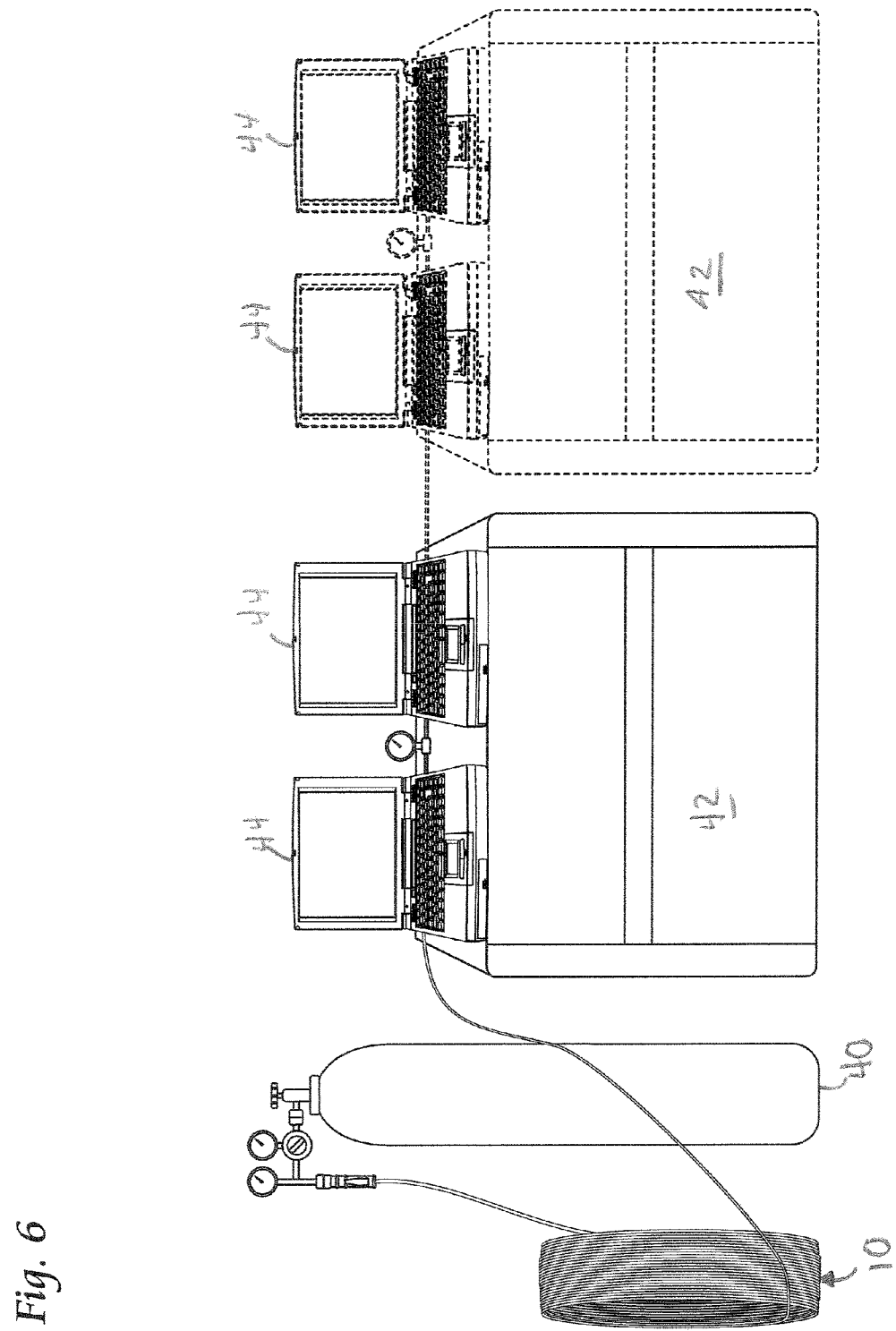
FIG. 6 is an operational view of the method of the invention, illustrating the air collection device connected at one end to a source of calibrated gas and at the other end to one or more analytical instruments for a computer-implemented method.

The analyzing step comprises connecting one end of the air collection device 10 as shown in FIG. 1 to a high pressure source of a reference gas mixture 40 and the other end of the air collection device to one or more analytical instruments 42 as shown in FIG. 6. The valves 14 or endcaps are in the open position. The calibrated gas is push gas that may be made using reference gas mixtures for calibrations, purchased from specialty gas companies, or from national metrology laboratories, such as the U.S. National Institute of Standards and Technology. The initial pressure of the calibrated gas is typically 2000 psi (pounds/sq. inch) which decreases slowly as the gas is used and the cylinder empties. A controlled pressure slightly above ambient pressure is used to gradually (slowly) push the air sample out of the air collection device. A flow rate of about 100 to about 200 cubic centimeters per minute, preferably 200 cubic centimeters per minute may be used.

The molecular diffusion rate varies with temperature, pressure and gas species. For carbon dioxide at sea level, it is on the order of 1.5 meter in both directions per day. Molecular diffusion rates at 290° K for many different gases are known. Also known is that diffusion slowly smoothes concentration mole fraction differences in the profile as time progresses. The following exemplary table shows how an initially extremely sharp spike in the CO2 mole fraction at one point in the coil gets smeared out over time, expressed as the characteristic full width (it is an exponential fall-off) of the concentration "bulge" that develops from the initial spike:

1 hour 0.64 m
6 hours after collection 1.6 m
1 day after collection 3.1 m
1 week after collection 8.3 m
1 year after collection 60 m The table provides that 6 hours after collection the resolution is ~1.6 m, or that for a 150 m long coil, there are 150/1.6=94 independent measurements available in the coil. The lower the resolution number, the greater the resolution. This gives an idea of how long after the descent (i.e. after collection) that the gas analysis must be done to avoid unacceptable degrading of the resolution of the mole fraction profile. This is also a function of tubing length and for the lengths as described, the analysis may be done up to a few days after the sample is collected. For longer tubing, one can wait longer after collection until analysis and not suffer as much loss in resolution.

The one or more analytical instruments 42 may be any standard analytical instrument known to measure the mole fraction of trace gases, otherwise known as trace gas analyzers. The one or more analytical instruments may be encased in Styrofoam to keep a constant temperature. An exemplary modified CO2 analyzer is a version of the AOS CO2 Airborne Analyzer System, produced by Atmospheric Observing Systems, Inc. (Boulder, Colo.). The AOS CO2 Airborne Analyzer System includes a small and very efficiently flushed cell in which the infrared absorption by CO2 is measured. This reduces the amount of gas needed to make a measurement of the CO2 mole fraction. The more gas that is used for the measurement, the more the vertical resolution of the measurement is degraded. It is to be appreciated that other trace gas analyzers may be used within the confines of the invention.

The high pressure reference gas mixture slowly pushes the air out of the air collection device into the one or more analytical instruments. This analysis or "read out" yields a continuous profile of the mole fraction of the gases being analyzed and this profile can have very high vertical resolution depending on the length of the air collection device.

To measure the mole fraction of multiple trace gases, the one or more analytical instruments 42 or analyzers may be used in series as shown in FIG. 6. Alternatively, a connector (not shown) may be used to connect the air collection device to multiple analytical instruments, although some resolution may be lost with this configuration. When arranged in this manner, each analyzer measures the mole fraction of one or several trace gases, depending on analyzer design. As the air is pushed through the analytical instrumentation, it could be pushed into another similar or a different type of instrument after it leaves the analysis cell, again with little loss of resolution. The sample could then be analyzed by other instruments that have the same or different requirements for injection, sample size, etc. The analysis can be done in steps in stop-flow mode, or continuously, depending on the requirements of the analytical instruments used. When obtaining high accuracy measurement data, a common practice is to frequently compare the signal recorded during analysis with the signal produced in the same instrument by a reference gas mixture with known mole fraction(s) of the trace gas(es) being measured. The data is displayed on a computer display 44 as mole fraction levels at different vertical positions in the atmosphere as shown in FIG. 6. This is computer-implemented.

Experimental Methods

Figure 7:
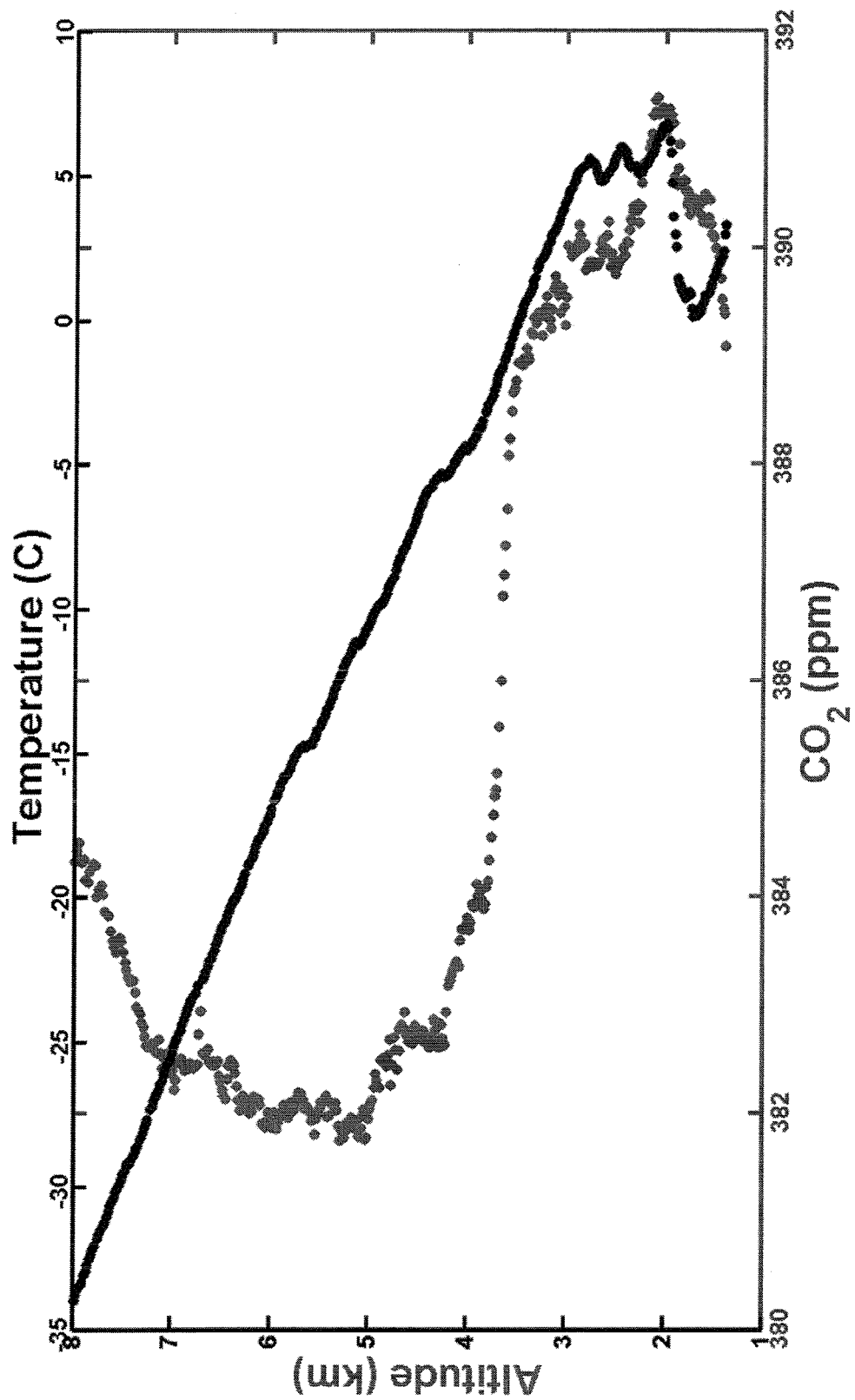
FIG. 7 is a plot of the lower part of an exemplary CO2 profile with temperature.
Figure 8:
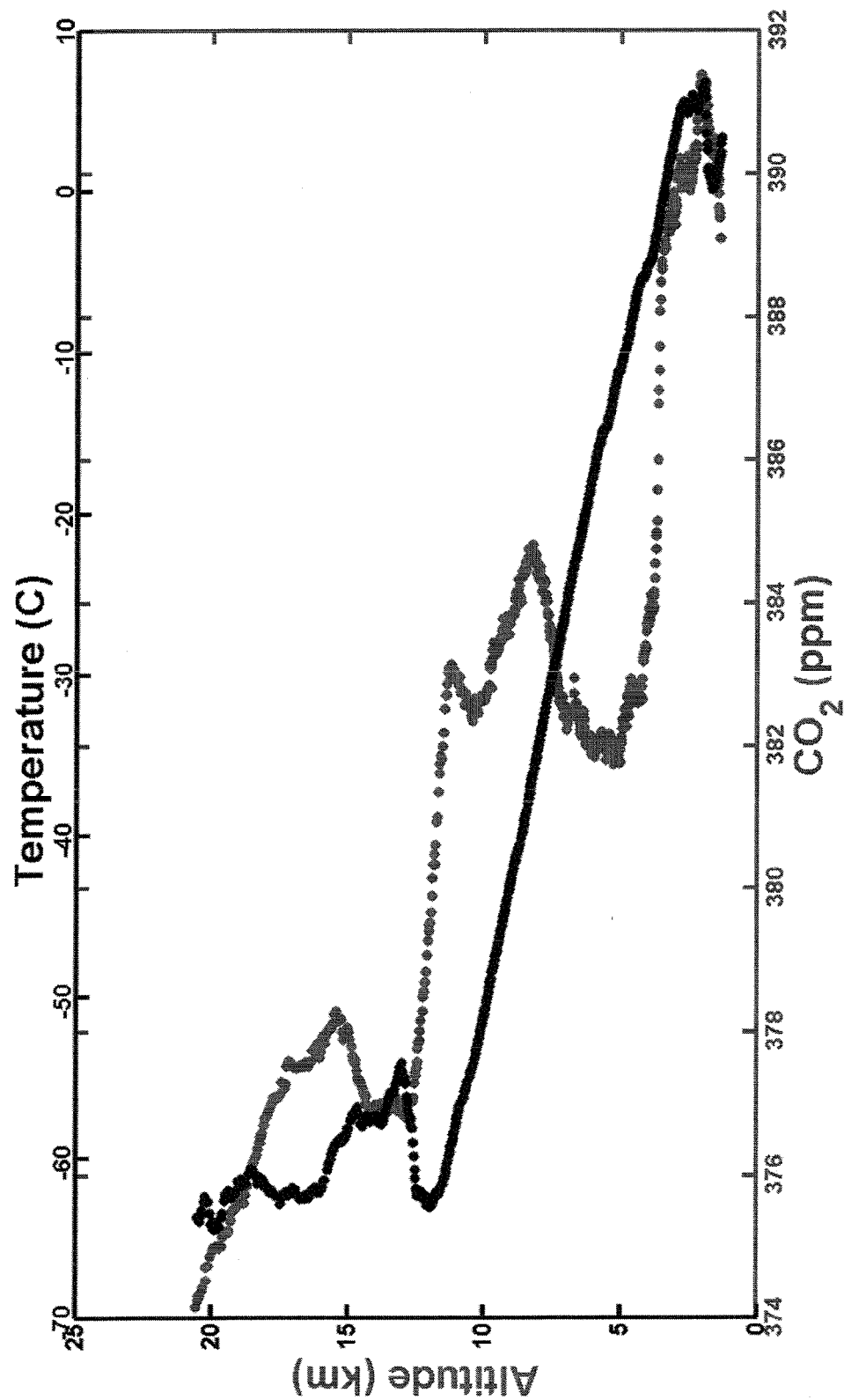
FIG. 8 is a plot of the entire exemplary CO2 profile of FIG. 7 with temperature.
Figure 9:
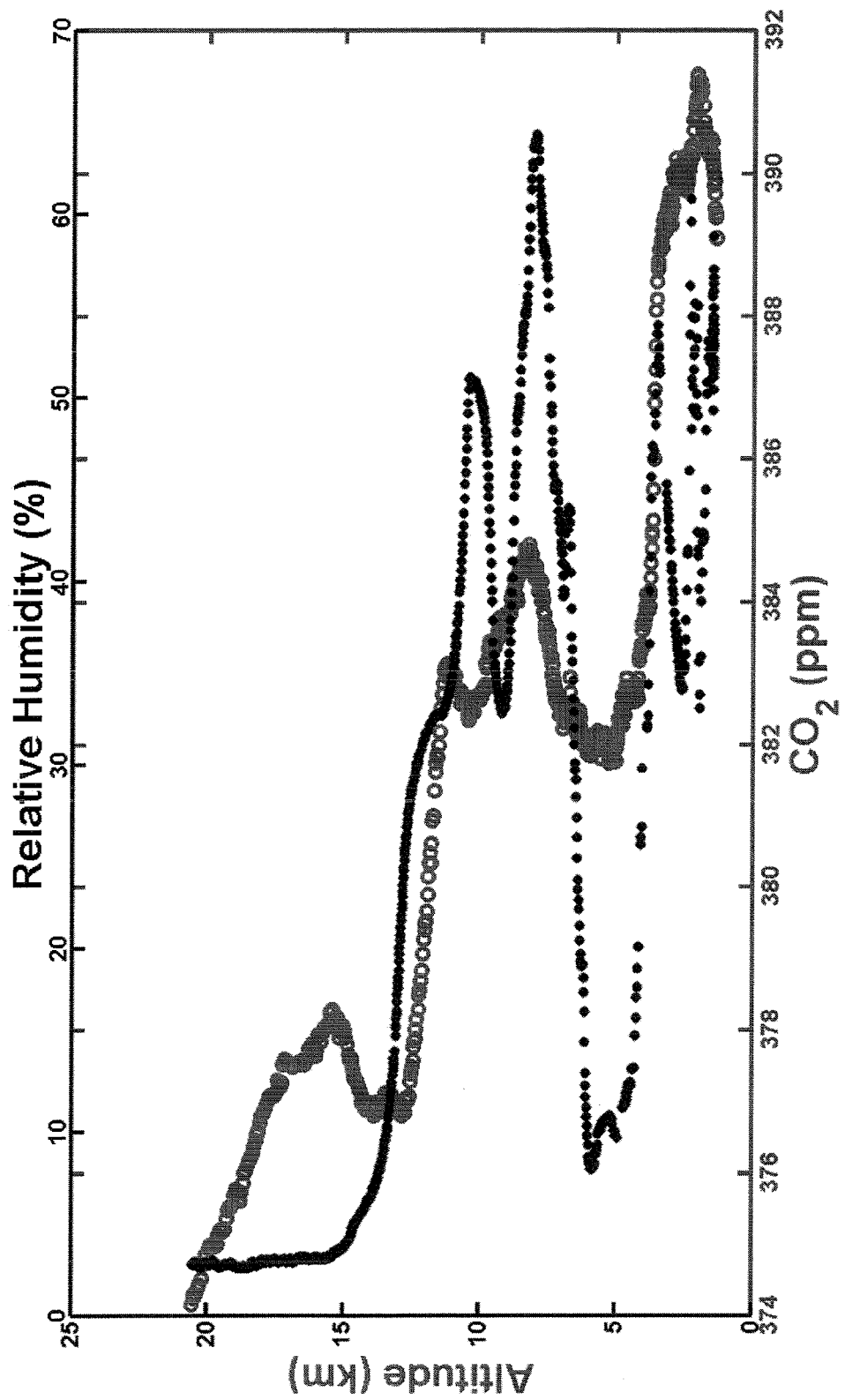
FIG. 9 is a plot of the entire exemplary CO2 profile of FIGS. 7 and 8 with relative humidity (RH)

The encased air collection device was successfully launched to about 20,000 m altitude by a helium-filled balloon. Cushion means of 54 practice golf balls tied together by 24 lateral loops of nylon string, 4 longitudinal loops and 8 diagonal loops was used. The balloon used was a 3000 gram latex balloon similar to those manufactured by Kaymont Corp. (Hunington Station, N.Y.). The total payload weighed 25.3 lbs. The ascent rate was estimated to be 1000 feet per minute and the average descent rate in the troposphere was estimated to be 950 feet per minute. The parachute was 10 feet in diameter The tracking of the air collection device during flight was done by a Global Positioning System (GPS) receiver on the balloon flight line and the location data radioed back to the ground. The collected continuous air sample was then analyzed for greenhouse gas mole fraction. From this experiment, it was found that by analyzing the coil several hours after the flight, there was a vertical resolution of about 80 m near the surface of the earth and that the resolution gradually degraded with increasing altitude. For example, at 10 km the vertical resolution of the profile was about 200 m and at 20 km, it was 0.9 km. This is well understood because the resolution in the atmosphere is approximately constant in density coordinates, not in geometric coordinates. If the coil had been 300 m long instead of 150 m long, the resolution would have been improved by a factor of two everywhere. The profiles are presented in FIGS. 7-9. These profiles use the temperature and pressure to correct for the effective volume at each altitude recorded assuming that the temperature of the air inside the coil is keeping up with that measured by the data collection device temperature measurement.

Figure 10:
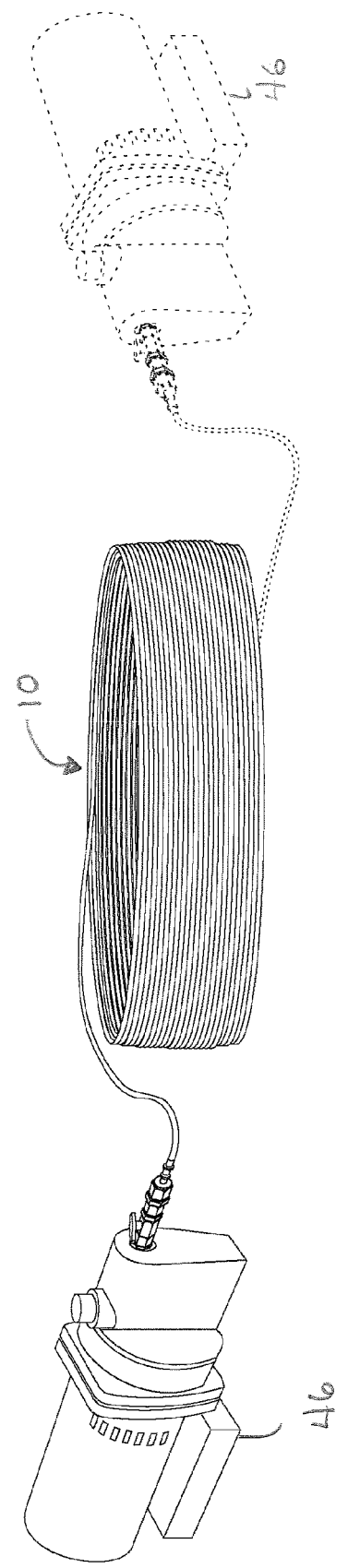
FIG. 10 is an operational view of another embodiment of the invention, illustrating at compressor at one end of an air collection device to draw or push gas therein for storage, and another compressor shown in dotted lines to illustrate alternative positioning.

In another embodiment, as illustrated in FIG. 10, the air collection device may also be used to store a time history of sample gas produced in the laboratory or elsewhere. As used herein and in the claims, the "air" collected in the air collection device includes both atmospheric air in the traditional sense (i.e. a mixture of gases) as well as the sample gas. As the gas sample is produced, a specialized compressor or pump 46 that is capable of producing very low and controlled pressure is used to slowly draw or push the gas sample into one of the open ends of the air collection device 10. The other end is also open. The compressor or pump 46 may be at either of the open ends, as indicated by dotted lines in FIG. 10. At a flow rate of about 5 cc/second, it could take 15 minutes to more than an hour to fill the small diameter elongated hollow tubing of the air collection device, depending on its length and diameter. If the flow rate and length of the elongated hollow tubing are such that it takes one hour for the air to flow through the elongated hollow tubing, after one hour the elongated hollow tubing holds a time-ordered record of the mole fraction of trace gases produced during the past hour. The compressor/pump 46 may run for the length of time for which the time history is obtained. Once the gas sample for the selected time period is in the air collection device, both ends thereof may be closed by turning the valve levers to a closed position or by positioning endcaps or the like on the open ends. This stores the gas within the air collection device. The gas sample may thereafter be analyzed in the same manner as the atmospheric air in the air collection device as described above. A possible miniature gas pump for this application would be Model NMP05, made by KNF Neuberger, Two Black Forest Road, Trenton, N.J. 08691. Other companies manufacture pumps with similar capabilities. The gas that may be stored in the air collection device may be nonreactive gases, including but not limited to, trace gases.

From the foregoing, it is to be appreciated that the system and method are a breakthrough in trace gas mole fraction measurements because of their simple design, operation, relatively low cost, and general ease with which vertically continuous profiles and time histories may be obtained using the air collection device. The system and method reduce costs, increase reliability, resolution and accuracy of measuring vertical profiles of certain gases in the free atmosphere, thus aiding in the understanding of global warming. The system and method permit bringing a continuous air sample from the atmosphere back to the laboratory for more precise measurements than would in many cases be obtained under less than ideal non-laboratory field conditions. The vertical resolution can be on the order of tens of meters in the lower atmosphere which is much better than generally achieved by flask sampling. The system and method provide enormous potential to collect inexpensively on a daily basis around the globe a substantially unlimited number of atmospheric profiles of a wide range of trace gases. The system and method acquire a continuous vertical profile of air using only one container, no other attached apparatus, and just one laboratory analysis. The system and method permit multiple profiles of CO2 and other trace gases to play an essential role in the validation of satellite observations and the improvement of atmospheric transport models as well as models of the biogeochemical cycles influencing the trace gases.

Although a particular embodiment of the invention has been described in detail for purposes of illustration, various modifications may be made without departing from the spirit and scope of the invention. Accordingly, the invention is not to be limited, except as by the appended claims.

I claim:

1. A method for using an air collection device to provide mole fraction measurements of at least one trace gas in the atmosphere, comprising the step of:
   Collecting in an air collection device a continuous air sample as a function of altitude, the air collection device comprised of elongated hollow tubing and a valve at each of the ends thereof for controlling the flow of air into and out of the air collection device with one of the valves remaining closed and the other valve being opened at the beginning or end of the ascent and being closed substantially at the end of the descent to seal the continuous air sample in the air collection device for measurement.

2. The method of claim 1, further comprising the step of:
   Analyzing the mole fraction of the at least one trace gas in the continuous air sample collected in the air collection device to provide vertical profile measurements of the at least one trace gas in the atmosphere.

3. The method of claim 1, wherein the elongated hollow tubing has an internal diameter in the range of about 0.230 inches to about 0.355 inches and a length in the range of about 50 m to about 300 m.

4. The method of claim 1, wherein the elongated hollow tubing is coiled.

5. The method of claim 1, wherein the air collection device further comprises insulation as an outer covering thereof.

6. The method of claim 5, wherein the air collection device ascends by balloon to a maximum altitude before descent and further comprising cushion means for protecting the air collection device upon landing and a plastic tube at an inlet side of the valve, wherein the valve is opened at the beginning or end of the ascent and is closed substantially at the end of the descent to substantially prevent dirt and other debris from contaminating the collected continuous air sample upon landing.

7. A method of using an air collection device to measure the mole fraction of at least one trace gas at different altitudes in the atmosphere, comprising the steps of:
   Transporting to a maximum altitude an air collection device comprised of at least one coil of small diameter elongated hollow tubing and closure means at each end for controlling the flow of air into and out of the air collection device, with one of the ends of the air collection device closed during flight and the other of the ends opened at the beginning or end of the ascent;
   collecting a continuous air sample through the open end of the air collection device as it descends from the maximum altitude to a minimum altitude, wherein the air sample remains unmixed within the tubing, the tubing diameter mitigating turbulent diffusion within the tubing;
   tracking the air collection device during its ascent and descent;
   closing the open end of the elongated hollow tubing substantially upon completion of the descent; and
   analyzing the continuous air sample collected within the air collection device to measure the mole fraction of the at least one trace gas at the different altitudes in the atmosphere.

8. The method of claim 7, wherein the analyzing step comprises the steps of:
   connecting one end of the air collection device to a source of calibrated air and the other end to at least one analytical instrument;
   pushing calibrated air through the air collection device into at least one analyzer to measure the mole fraction of the at least one trace gas in the collected continuous air sample.

9. The method of claim 8, wherein the calibrated air is pushed into the air collection device at a rate of about 100 to about 200 cubic centimeters per minute.

10. The method of claim 7, wherein the elongated hollow tubing has an internal diameter in the range of about 0.230 inches to about 0.355 inches and a length in the range of about 50 m to about 300 m.

11. The method of claim 7, wherein the air collection device further comprises insulation.

12. The method of claim 11, wherein the air collection device is transported by a balloon to the maximum altitude, the air collection device further comprising cushion means for protecting the air collection device from impact forces during landing.

* * * * *